(12) United States Patent
Milojevic et al.

(10) Patent No.: US 7,328,072 B2
(45) Date of Patent: Feb. 5, 2008

(54) TELESCOPIC ARRAY FOR A COCHLEAR IMPLANT

(75) Inventors: Dusan Milojevic, Lane Cove (AU); John Parker, Lane Cove (AU)

(73) Assignee: Cochlear Limited, Lane Cove, New South Wales (AU)

( * ) Notice: Subject to any disclaimer, the term of this patent is extended or adjusted under 35 U.S.C. 154(b) by 537 days.

(21) Appl. No.: 10/785,485

(22) Filed: Feb. 23, 2004

(65) Prior Publication Data
US 2004/0225336 A1    Nov. 11, 2004

(30) Foreign Application Priority Data
Feb. 21, 2003 (AU) .............................. 2003900773

(51) Int. Cl.
*A61N 1/05* (2006.01)
(52) U.S. Cl. .................... 607/137; 607/57; 606/108
(58) Field of Classification Search .................. 607/57, 607/3, 116, 137; 606/108
See application file for complete search history.

(56) References Cited
U.S. PATENT DOCUMENTS

| 4,261,372 | A | * | 4/1981 | Hansen et al. | ............... 607/137 |
| 4,532,930 | A | | 8/1985 | Crosby et al. | |
| 5,720,099 | A | | 2/1998 | Parker et al. | |
| 6,309,410 | B1 | * | 10/2001 | Kuzma et al. | ............... 607/137 |
| 6,968,238 | B1 | * | 11/2005 | Kuzma | ............... 607/137 |
| 2003/0125785 | A1 | * | 7/2003 | Kuzma et al. | ............... 607/116 |

* cited by examiner

*Primary Examiner*—Kennedy J. Schaetzle
(74) *Attorney, Agent, or Firm*—Christie, Parker & Hale, LLP (57) ABSTRACT

A cochlear implant device that has an elongate member with electrode(s) supported thereon. The elongate member comprises a first portion that is insertable into the implantee and at least one second portion wherein, on or following insertion of the first portion, the second portion is at least partially supported by the first portion. During or after insertion of the first portion, the second portion is movable relative to the first portion.

11 Claims, 5 Drawing Sheets

TELESCOPIC ARRAY FOR A COCHLEAR IMPLANT

CROSS-REFERENCE TO RELATED APPLICATION

This application claims priority of Australian Patent Application Number 2003900773, filed on Feb. 21, 2003.

1. Field of the Invention

The present invention relates to an implantable device and, in particular, to a tissue-stimulating device such as a cochlear implant electrode array.

2. Background of the Invention

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely an external component commonly referred to as a processor unit, and an implanted internal component commonly referred to as a receiver/stimulator unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted receiver/stimulator unit situated within a recess of the temporal bone of the implantee. This transcutaneous transmission occurs through use of an inductive coupling provided between the external antenna transmitter coil which is positioned to communicate with an implanted antenna receiver coil provided with the receiver/stimulator unit. This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit typically included the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a stimulating signal within a preselected frequency range to the appropriate cochlea region. The electrical currents and electric fields from each electrode stimulate the nerves disposed on the modiolus of the cochlea.

It has been found that in order for these electrodes to be effective, the magnitude of the currents flowing from these electrodes and the intensity of the corresponding electric fields, are a function of the distance between the electrodes and the modiolus. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiolus as small as possible. This is best accomplished by providing the electrode array in a shape which generally follows the shape of the modiolus. Also, this way the delivery of the electrical stimulation to the auditory nerve is most effective as the electrode contacts are as close to the auditory nerves that are particularly responsive to selected pitches of sound waves.

Early cochlear implant electrode arrays were constructed in a straight configuration with the natural shape of the cochlea dictating the trajectory of the electrode array during insertion. Such electrode arrays have proven effective in providing the sensation of hearing to recipients however the final position of such electrode arrays following insertion has often been found to be remote from the modiolus and along the outside wall of the cochlea.

In order to achieve an electrode array position close to the inside wall of the cochlea, the electrode assembly can be designed such that it assumes this position upon or immediately following insertion into the cochlea. This is a challenge as the assembly needs to be shaped such that it assumes a curved shape to conform with the shape of the modiolus and must also be shaped such that the insertion process causes minimal trauma to the sensitive structures of the cochlea. In this regard, it has been found to be desirable that the electrode assembly be generally straight during the insertion procedure.

Several procedures have been adopted to provide an electrode assembly that is relatively straight during initial insertion while adopting a curved configuration following insertion in the cochlea. In one case, the electrode array is manufactured in a conventional straight configuration and inserted in the conventional manner and an additional positioner element is additionally inserted behind the electrode array to urge the array against the inside wall of the cochlea. Such a method is based upon the principle of the positioner filling the cochlea space behind the electrode array to force the electrode array against the inner wall of the cochlea and as such increases the potential of damage being caused to the sensitive structures of the cochlea and greatly affects the natural hydrodynamic nature of the cochlea. More recently, it has also been suspected that such a method may also increase the incidence of meningitis and infection to the cochlea by providing a space between the positioner and electrode array which may be an avenue for infection to enter the cochlea.

A more preferred procedure is to provide a platinum wire stylet to hold a pre-curved electrode assembly in a generally straight configuration up until insertion. The platinum wire is inserted into a lumen or channel located in the pre-curved electrode assembly with such lumen/channel allowing a passageway to accommodate the stylet. During or immediately following insertion, the platinum stylet is withdrawn allowing the assembly to return to its pre-curved configuration and assume a final position close to the inside wall of the cochlea.

It is desired to provide an alternative arrangement for achieving close positioning of stimulating electrodes to the inside wall of the cochlea, while minimising trauma to the sensitive structures of the cochlea.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an implantable tissue-stimulating device for an implantee comprising an elongate member having at least one electrode supported thereon, the elongate member comprising:

a first portion having a proximal end and a distal end, the first portion being insertable into the implantee; and at least one second portion having a proximal end and a distal end;

wherein, on or following insertion of the first portion, the second portion is at least partially supported by the first portion;

and further wherein, during or after insertion of the first portion, the second portion is movable relative to the first portion such that the distal end of the second portion is moved away from the proximal end of the first portion.

In a preferred embodiment, the implantable device is a cochlear implant device that is adapted for insertion into the cochlea of an implantee. Preferably, the device is adapted for insertion through a cochleostomy and into the scala tympani of the cochlea of the implantee. Where appropriate, the device will be described below with reference to its particular preferred application of placement in the cochlea. It should, however, be appreciated that the device could be implanted in other locations within an implantee.

In one embodiment, the first portion is preferably insertable into and then supported by the tissue of the implantee. For example, in the case of insertion into the cochlea, the first portion is preferably inserted through the cochleostomy.

In one embodiment, the first portion preferably has a length such that, on insertion, its proximal end is positioned at or adjacent the cochleostomy and its distal end is positioned short of or relatively close to the first basal turn of the cochlea.

In one embodiment, the first portion of the elongate member is substantially straight. The first portion can comprise a tube comprising at least one sidewall extending from the proximal end to the distal end. The tube can be a full tube and hence be closed except at its proximal and distal ends. In another embodiment, the tube can be a partial tube. In this case, the tube can have one or more openings in its one or more sidewalls. For example, the tube can have a longitudinal slit or slot extending for a portion or all of the length of the tube.

In a further embodiment, the first portion can be cylindrical. In another embodiment, the tube can be multi-sided and hence have a non-circular cross-section. In a still further embodiment, the cross-section can be substantially circular or oval in cross-section.

In yet a further embodiment, the first portion is formed of a material that ensures that the first portion retains its configuration following insertion in the implantee. If the first portion is straight, it preferably remains straight following insertion. In one embodiment, the first portion can be formed of a suitable biocompatible material. In one embodiment, the material can be a suitable polymeric or elastomeric material, such as a silicone, a polyurethane, or a polyimide.

As described, the second portion is at least partially supported by the first portion on or following insertion of the first portion. In this regard, the device can be manufactured and packaged such that the second portion is at least partially supported by the first portion on delivery to the surgeon who will implant the device. In another embodiment, the device can be assembled just prior to implantation with the second portion only being supported by the first portion at a time relatively close to implantation of the device. In yet a further embodiment, the first portion may be inserted as a first step. The second portion can then be brought into a position such that it is supported by the first portion prior to the subsequent movement of the second portion relative to the first portion.

In a still further embodiment, the second portion may be supported within the first portion. Where the first portion is a tube, the second portion is preferably sized and shaped such that it can pass into the tube and be supported therein.

In one embodiment, following insertion of the first portion and with the second portion supported by the first portion, the second portion is then preferably moved forwardly out of the distal end of the first portion. This movement preferably results in the second portion travelling further into the implantee, for example, further into the cochlea. Once fully deployed, the proximal end of the second portion may be located within the first portion. In another embodiment, the respective proximal ends of the first and second portions can be substantially or precisely aligned following deployment of the second portion. In yet another embodiment, the second portion can extend from its proximal end that is positioned outside the proximal end of the first portion, through the first portion, and to its distal end that is outside the distal end of the distal end of the first portion.

In one embodiment, the second portion can be pre-formed so that at least a portion thereof extending back from its distal end adopts a different configuration to that of the first portion following its deployment from the distal end of the first portion. In one embodiment, the second portion is preferably pre-formed so that said portion adopts a curved configuration following deployment from the first portion. The pre-formed configuration can result in said portion of the second portion adopting a spirally curved configuration. The second portion preferably has an inner surface that, following deployment, substantially conforms with the modiolar wall of the cochlea.

In a further embodiment, the degree of movement of the second portion relative to the first portion is controllable. In one embodiment, the extent of deployment of the second portion into the implantee from the first portion is also controllable. In this regard, the device can be constructed so as to prevent deployment of the second portion beyond a predetermined depth into the cochlea.

In one embodiment where the first portion comprises a tube, the diameter of the tube preferably decreases at least adjacent its distal end. In one embodiment, the diameter of the tube can smoothly taper at least adjacent its distal end. In this embodiment, the diameter of the second portion preferably expands at a predetermined location spaced from the distal end of the second portion. In this way, the second portion is free to be deployed from the first portion until frictional engagement between the expanded diameter of the second portion and the tapering constriction of the tube prevents further deployment.

This increase in frictional engagement should be able to be felt by the surgeon implanting the device and so alert the surgeon to the probability that maximum insertion depth of the second portion has been reached. The second portion can have one or more markers, such as visual markers, on its outer wall to also provide an indication of the depth of insertion of the second portion relative to the first portion into the cochlea.

In some embodiments of the device, a lumen is not required in the second portion of the elongate member to ensure appropriate implantation of the device. Despite this, the second portion can be provided with a lumen if desired. The lumen can extend from an opening in the second portion for at least some distance into the second portion. In one embodiment, the lumen can extend from an opening positioned at or adjacent the proximal end of the second portion through the second portion.

Such a lumen can be used as a channel or reservoir for the delivery of bio-active substances into the cochlea of the implantee. In one embodiment, the bio-active substance in the reservoir can leach from the lumen into the surrounding material of the second portion and eventually migrate out of the device to the desired site of action for the bio-active substance. In another embodiment, the second portion can have one or more substance egress means whereby the bio-active substance can move out of the lumen and through the body of the second portion to a position that is preferably close to the desired site of action for the bio-active substance.

Where the bio-active substance is carried in or comprises a fluid, each substance egress means preferably comprises a fluid egress means.

Each fluid egress means preferably has a valve means that allows fluid to exit the lumen but prevents, or at least substantially prevents, fluid flow from external the elongate member back into the lumen.

In a further embodiment, the proximal opening of the lumen can be in fluid communication with an additional reservoir for the bio-active substance that is external to the device. A pumping means, such as an osmotic pump, can transfer the bio-active substance from the additional reservoir into the lumen for subsequent delivery to the appropriate site of action.

It is also envisaged that the bio-active substance can be captured in the form of a solid pellet. For example, the bio-active substance may be impregnated in a ceramic or a polymer pellet. The bioactive substance may, therefore, be released at a predetermined rate. This solid pellet can then be stored in the lumen reservoir or in an external reservoir connectable to the lumen.

In one embodiment, the bioactive substance can comprise a steroid. In another embodiment, the bioactive substance can perform a function of reducing the resting neuron potential of neurons within the cochlea. The use of such substances can result in less energy being required to excite the neurons and cause stimulation. In yet another embodiment, the bioactive substance can comprise a nerve growth factor and mimetics to enhance the survival and growth of the nerve cells in the cochlea and to thereby improve the performance of the cochlear implant.

As a stylet positioned in the lumen is not necessarily required for implantation of the device, the osmotic pump and tube connecting the pump to the lumen can be mounted to the lumen at the time of manufacture of the device. This has the potential advantage of ensuring no connections need be made between the pump, the tube, and/or the opening in the lumen at the time of implantation of the device. This simplifies the surgery and also reduces the likelihood of inappropriate or inadequate installation of the pump to the lumen.

In a still further embodiment, the second portion is preferably free to be moved relative to the first portion, at least until maximum insertion depth is reached as described above. In one embodiment, the surface of the first portion and/or the surface of the second portion that could come into contact with each other during desired movement of the second portion are coated with a lubricious material. Where the first portion is a tube, the inner surface of the tube can be coated with the lubricious material.

The lubricious material typically becomes lubricious on being brought into contact with a fluid, such as a saline solution. Still further, the coating typically become lubricious on being brought into contact with a body fluid, such as cochlear fluid.

In one embodiment, the lubricious material is selected from the group consisting of polyacrylic acid (PAA), polyvinyl alcohol (PVA), polylactic acid (PLA) and polyglycolic acid (PGA). It is envisaged that other similar materials could also be used.

In another embodiment, the contact area between the surface of the first portion and the surface of the second portion is minimised to reduce the friction between the surfaces and so allow relatively free movement of the second portion, until at least the desired maximum extent of insertion of the second portion is reached.

In one embodiment, the inner surface of a tubular first portion and/or a portion of the outer surface of the second portion can be patterned to minimise the contact area. For example, the pattern can comprise a series of ridges and/or grooves. In another embodiment, the role of the ridges can be provided by a number of separate guidewires extending longitudinally and positioned between the inner surface of the tube and the outer surface of the second portion. Still further, one or more guidewires could extend spirally through the tube and be adapted to be positioned between the respective surfaces.

In one embodiment, said at least one electrode is provided on the second portion of the elongate member. In another embodiment, said at least one electrode is provided on the first portion of the elongate member. Still further, one or more electrodes can be provided on both the first portion and the second portion of the elongate member.

Where the first and second portions have a plurality of electrodes, the electrodes are preferably aligned along these portions. In a further embodiment, the alignment of the electrodes of the second portion substantially matches that of the electrodes on the first portion. In this regard, a guide means can be provided to ensure that the respective sets of electrodes of the two portions are aligned following deployment. For example, the inner surface of the tubular first portion may have a ridge or groove that is adapted to engage a corresponding complementary groove or ridge on the outer surface of the second portion.

Once implanted, the one or more electrodes mounted on the member, if present, can receive stimulation signals from a stimulator device. The stimulator device is preferably electrically connected to the elongate member by way of an electrical lead. The lead can include the one or more wires extending from each electrode of the array mounted on the elongate member.

In one embodiment, the lead can extend from the elongate member to the stimulator device or at least the housing thereof. In one embodiment, the lead is continuous with no electrical connectors, at least external the housing of the stimulator device, required to connect the wires extending from the electrodes to the stimulator device. One advantage of this arrangement is that there is no requirement for the surgeon implanting the device to make the necessary electrical connection between the wires extending from the electrodes and the stimulator device.

Where the first portion is a tube and has one or more electrodes mounted thereon, the wires extending from these electrodes are preferably encapsulated within the wall of the tube and extend at least back to the proximal end thereof. This results in the interior of the tube being free to receive the second portion without interference from the wires.

According to a further aspect, the present invention is a method of implanting a tissue-stimulating device in an implantee, said device comprising an elongate member having at least one electrode supported thereon, the elongate member comprising a first portion having a proximal end and a distal end, said first portion at least partially supporting at least one second portion during or after insertion of said first member, said second portion having a proximal end and a distal end, the second portion being movable relative to the first portion such that the distal end of the second portion is moved away from the proximal end of the first portion, the method comprising:

(a) forming an ostomy in the implantee;

(b) inserting the first portion of the elongate member through the ostomy and into the implantee;

(c) deploying the second portion of the device forwardly from the first portion and further into the implantee.

In a preferred embodiment of this aspect, the ostomy is a cochleostomy and the device is a cochlear implant for implantation in the cochlea of the implantee.

In one embodiment of this aspect, the second portion of the device can be supported by the first portion during insertion of the first portion into the implantee. Once the first portion is in position, the second portion can then be deployed.

The first portion is preferably substantially straight and, when inserted through a cochleostomy, causes the second portion to adopt a substantially straight configuration. This enables ease of insertion of the second portion into the cochlea. As the second portion passes beyond the first portion, it is free to move from the forced substantially straight configuration to a second substantially curved configuration.

In one embodiment, the second portion can be deployed relatively quickly after insertion of the first portion and certainly during the same surgical procedure.

In another embodiment, the device can be implanted and the surgical procedure completed without deployment of the second portion. In this case, the second portion can be deployed in a separate procedure at a later time. Such a method can be usefully employed where an implantee requires a cochlear implant but is only suffering relatively high frequency deafness. In such cases, the implantee may benefit from receiving a cochlear implant that allows the auditory network of the implantee to receive high frequencies whilst leaving the remainder of the cochlea to act naturally to receive relatively lower or middle frequencies. In this case, a traditional hearing aid may be used to amplify relatively low and middle frequency sounds in conjunction with the cochlear implant.

In this case, the electrodes of the first portion are active only and deliver electrical stimulation to the basal portion of the cochlea. If the implantee suffers progressive hearing loss into the middle and relatively lower frequencies, the implantee can undergo a further procedure during which the second portion is deployed from the first portion so positioning electrodes far deeper into the cochlea and so allowing the auditory network to receive these frequencies. This is anticipated to be a far less damaging procedure to the cochlea than one that requires removal of a previously implanted short electrode and implantation of a new longer electrode.

BRIEF DESCRIPTION OF THE DRAWINGS

By way of example only, preferred embodiments of the invention are now described with reference to the accompanying drawings, in which.

DETAILED DESCRIPTION AND PREFERRED MODE OF CARRYING OUT THE INVENTION

Figure 1:
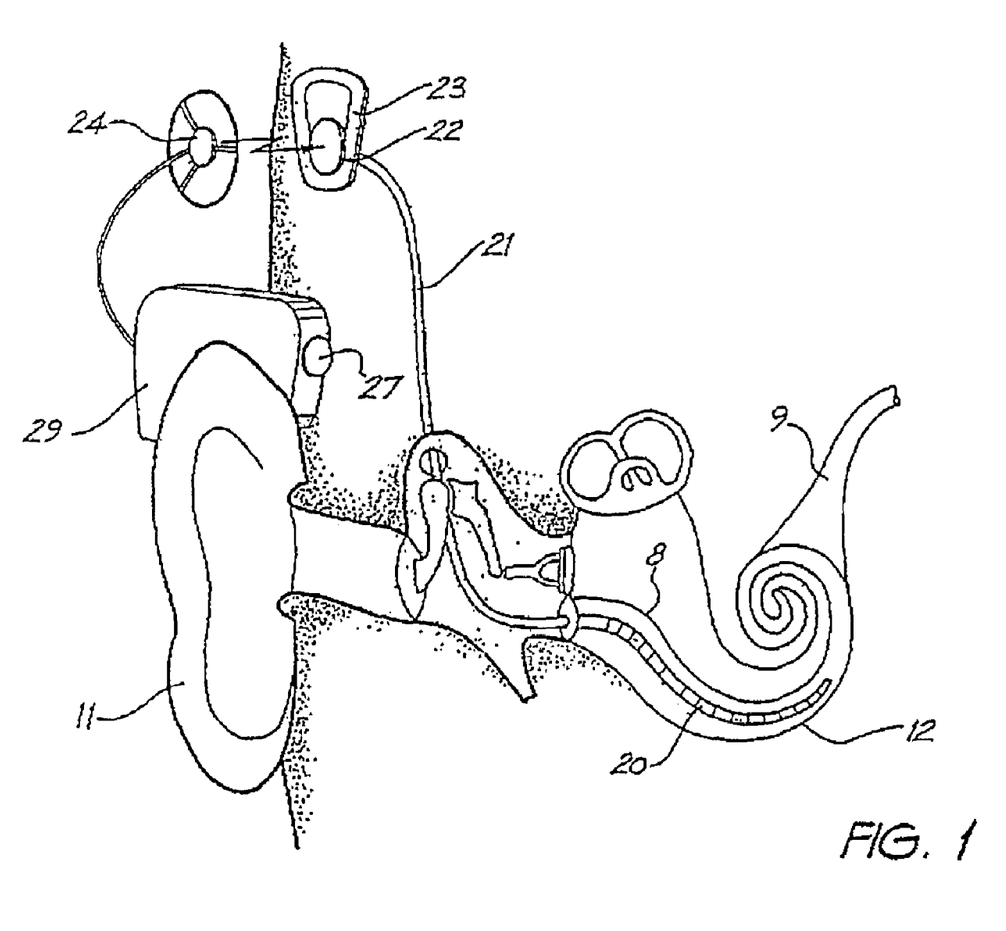
FIG. 1 is one example of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

Figure 2:
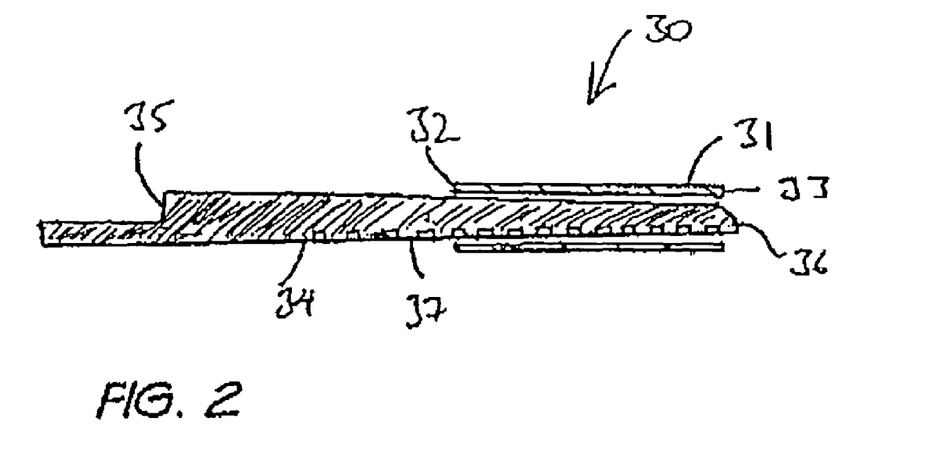
FIG. 2 is a cross-sectional view of one embodiment of a tissue-stimulating device of the present invention adapted for insertion in the cochlea of an implantee.

One embodiment of a cochlear implant electrode array for insertion through a cochleostomy and into the scala tympani 19 of the cochlea 12, according to the present invention, is depicted generally as 30 in FIG. 2. The elongate member 30 firstly comprises a substantially straight first portion 31 having a proximal end 32 and a distal end 33 that is insertable into the implantee. The elongate member 30 also comprises a second portion 34 which in turn has a proximal end 35 and a distal end 36. The proximal end 35 of the second portion is also connected to an auxiliary portion 38 as shown.

Figure 3:
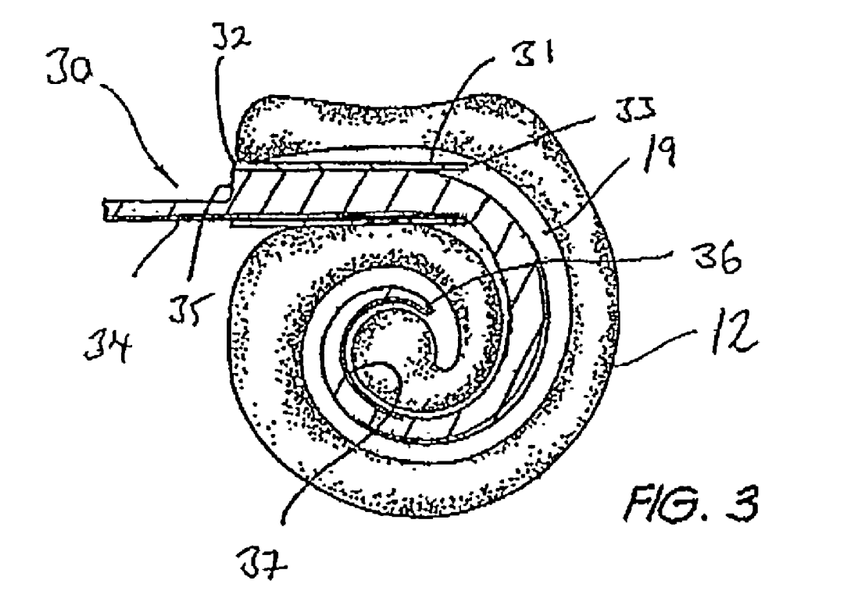
FIG. 3 depicts the device of FIG. 2 implanted in the cochlea.

As depicted in FIG. 3, the first portion 31 is insertable into the cochleostomy. In the depicted embodiment, the first portion 31 has a length such that on insertion its proximal end 32 is positioned at or adjacent the cochleostomy and its distal end 33 is positioned short of or relatively close to the first basal turn of the cochlea 12.

Figures 4A, 4B:
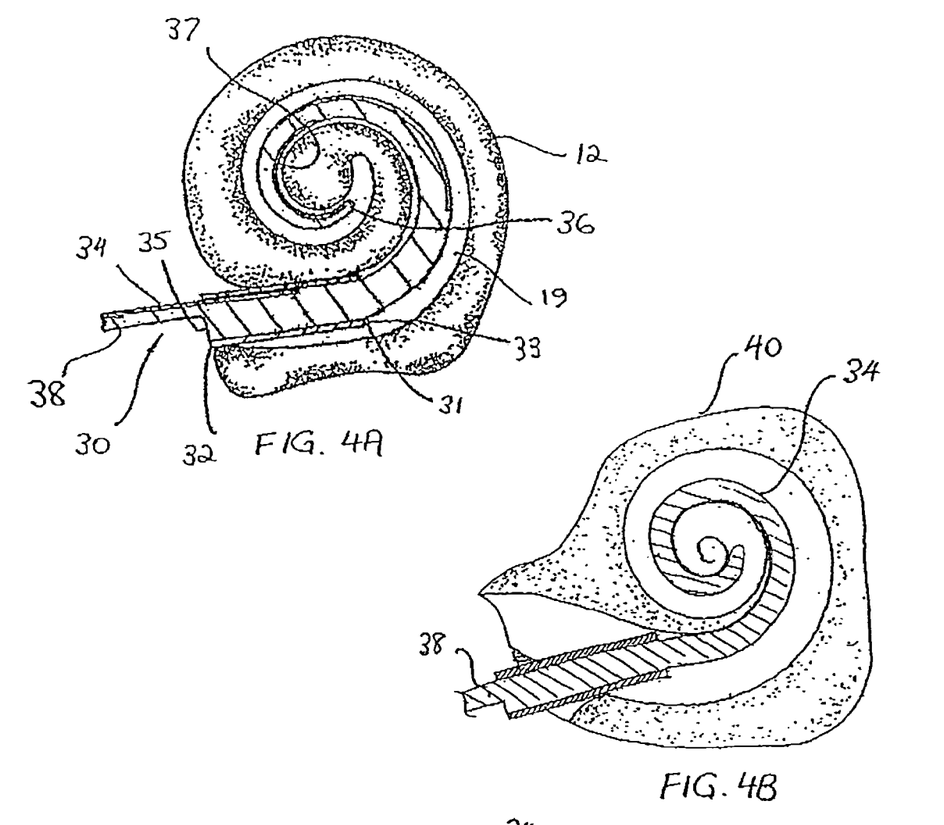
FIG. 4a depicts an alternative arrangement for the device of FIGS. 2 and 3.
FIG. 4b depicts a further alternative arrangement for the device of FIGS. 2 and 3.

Referring to FIG. 4*a*, the first portion 31 has a reduced length than that shown in FIG. 3 and so the distal end 33 is positioned just short of the first basal turn of the cochlea 12. This shorter first portion 31 also enables the region near the distal end 33 to remain in contact with the wall of the cochlea 12 as shown.

FIG. 4*b* shows the first portion 31 implanted in a cochlea 40 having a different anatomy and entry point than that shown in FIG. 4*a*.

Figure 4C:
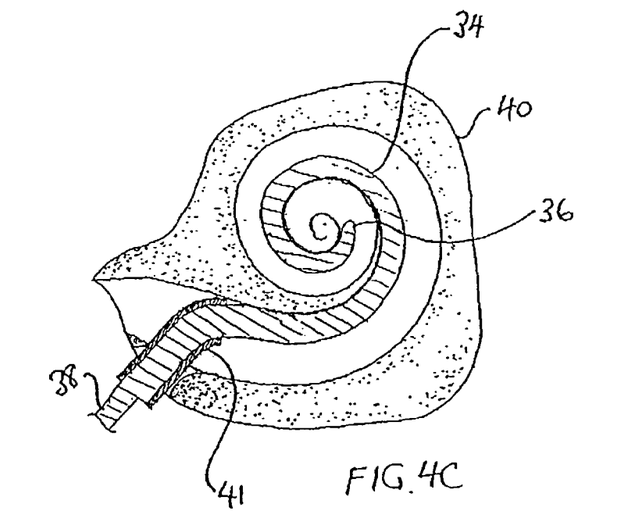
FIG. 4c depicts a further alternative arrangement for the device of FIGS. 2 and 3.

An alternative configuration for the first portion is shown in FIG. 4*c*, in which an end region of the first portion 41 is curved. This can advantageously facilitate insertion into the cochlea, through a smaller cochleostomy, since the curved end region can be inserted into the cochlea more perpendicularly. Moreover, the curved end region facilitates easier and potentially less traumatic insertion of the second portion 34, when being deployed through such smaller cochleostomies.

Also, more stimulation frequency coverage can be made, by positioning the active portion of the array near the modiolus in the basal region of the scala tympani.

In FIGS. 2 and 3, the first portion 31 comprises a cylindrical tube. In these drawings, the tube is to be understood as being a full tube and hence is closed except at its proximal and distal ends. In another embodiment, the tube can be a partial tube. In this case, the tube can have one or more openings in its one or more sidewalls. For example, the tube can have a longitudinal slit or slot extending for a portion or all of the length of the tube.

While the first portion depicted in FIGS. 2 and 3 is cylindrical, the tube can be multi-sided and hence have a non-circular cross-section. In a still further embodiment, the cross-section can be substantially circular or oval in cross-section.

The first portion 31 is formed of a material that ensures that it retains its configuration following implantation in the implantee. The first portion 31 can be formed of a suitable biocompatible material. In one embodiment, the material can be a suitable polymeric or elastomeric material, such as a silicone, a polyurethane, or a polyimide.

Figures 5A, 5B:
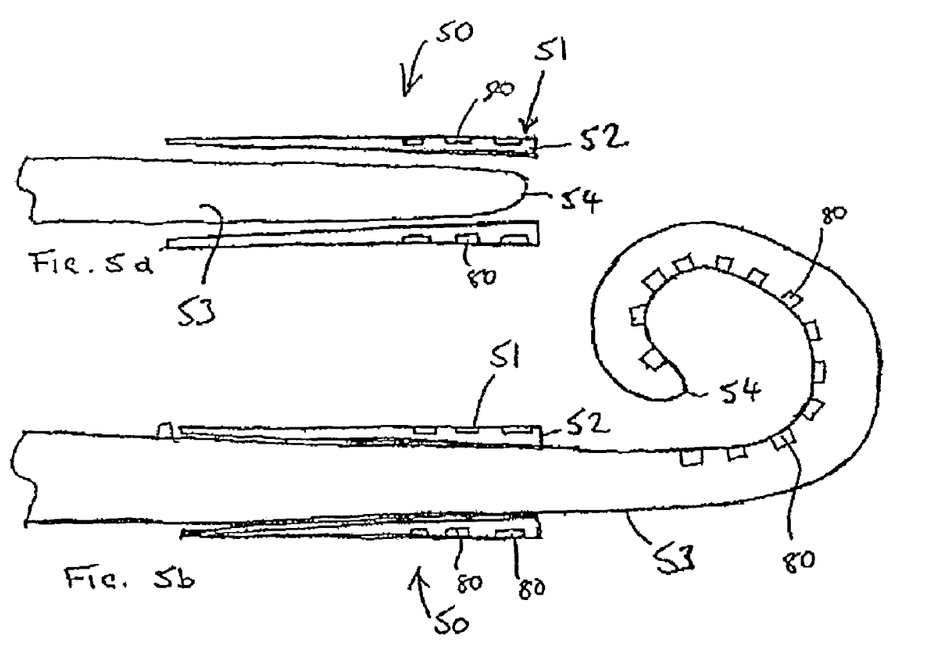
FIGS. 5a and 5b are cross-sectional views of another embodiment of a device according to the present invention.

As shown in FIGS. 5*a* and 5*b*, the first portion 31 may be provided with a plurality of stimulating electrode elements 80 positioned thereon, such that following implantation, the stimulating electrode elements 80 are positioned proximal to the inner wall of the cochlea. The number of stimulating electrode elements 80 provided on the first portion 31 can vary and the first portion may contain up to 6-8 electrodes along its length.

Whilst in the embodiment shown in FIGS. 2 and 3 the first portion 31 is shown as a short straight tube extending close to the first basal turn of the cochlea, it is also envisaged that the first portion 31 could extend slightly beyond the first basal turn. In such an embodiment, the first portion would be constructed with a slight curvature at its distal end to enable the first portion 31 to extend beyond the first turn and conform to the shape of the inner wall of the cochlea.

The second portion 34 is at least partially supported within the first portion 31 on or following insertion of the first portion in the cochlea 12. In this regard, the device 30 can be manufactured and packaged such that second portion 34 is at least partially supported within the first portion 31 on delivery to the surgeon who will implant the device 30. In another embodiment, the device 30 can be assembled just prior to implantation with the second portion 34 only being supported within the first portion 31 at a time relatively close to start of implantation of the device 30. In yet a further embodiment, the first portion 31 can be firstly implanted in the implantee. The second portion 34 can then be brought into a position such that it is supported within the first portion 31 prior to the relative movement of the second portion 34 to the first portion 31. Following insertion of the first portion 31 and with the second portion 34 supported thereby, the second portion 34 is then able to be moved forwardly out of the distal end 33 of the first portion 31. This movement results in the second portion 34 travelling further into the cochlea, as is depicted in FIG. 3. In the depicted embodiment, the second portion 34 is inserted until the proximal end 35 of the second portion 34 is substantially aligned with the proximal end 32 of the first portion 31.

It will be appreciated that in other circumstances, the proximal end 35 of the second portion 34 could end up located within the first portion 31 or positioned outside the proximal end 32 of the first portion 31. In such other circumstances the proximal end 35 of the second portion 34 could be provided with indicia means to represent the desired insertion depth to the surgeon In the depicted embodiment, the second portion 34 is pre-formed so that at least a portion thereof extending back from its distal end 36 preferentially adopts a spirally curved configuration on deployment from the first portion 31. The second portion 34 has an inner surface 37 that, following deployment, substantially conforms with the modiolar wall of the cochlea 12.

In use, the second portion 34 can be either fully or partially deployed relatively quickly after insertion of the first portion 31 and certainly during the same surgical procedure.

It should be appreciated, however, that the device 30 can be implanted and the surgical procedure completed without deployment of the second portion 34. In this case, the second portion 34 can be deployed in a separate procedure at a later time. Such a method can be usefully employed where an implantee requires a cochlear implant but is only suffering relatively high frequency deafness. In such cases, the implantee may benefit from receiving a cochlear implant that allows the auditory network of the implantee to receive high frequencies whilst leaving the remainder of the cochlea to act naturally to receive relatively lower or middle frequencies. In this case, a traditional hearing aid may be,used to amplify relatively low and middle frequency sounds in conjunction with the cochlear implant. As the first portion 31 is hollow and relatively thin walled, the presence of the first portion 31 in the cochlea will not greatly alter the hydrodynamic nature of the cochlea and interfere greatly with the natural hearing process required for detecting the lower frequency sounds.

In this case, the electrodes of the first portion 31 are active only and deliver electrical stimulation to the basal portion of the cochlea 12. If the implantee suffers progressive hearing loss into the middle and relatively lower frequencies, the implantee can undergo a further procedure during which the second portion 34 is either newly deployed from the first portion 31, or is extended from a partially deployed second portion that has been earlier implanted, so positioning electrodes far deeper into the cochlea 12 and so allowing the auditory network to receive these frequencies. This is anticipated to be a far less damaging procedure to the cochlea 12 than one that requires explantation of a previously implanted short electrode and implantation of a new longer electrode.

In contrast to the depicted embodiments, the second portion can be constructed such that it does not adopt a preferred configuration. In this case, the second portion is preferably constructed from a resiliently flexible material and is provided with a stylet-like shaping element that is positioned within the second portion and which directs the resiliently flexible material into a pre-formed curved configuration of the shaping element.

In this case, the second portion 34 is held straight while it is supported by the first portion 31. In this regard, it will be understood that the stylet-like shaping element is constructed so as to enable modification of the configuration of the second portion 34 but not the first portion of the elongate member.

As the second portion is deployed from the first portion, the stylet-like shaping element is able to influence the configuration of the second portion 34 and so force it to adopt its configuration. In the case of implantation into the cochlea, on initial deployment, the stylet-like shaping element causes a region adjacent distal end 36 of the second portion 34 to begin to curve so that the second portion 34 can travel around the basal turn of the cochlea 12 preferably without impacting the walls of the cochlea 12. As the second portion 34 is further deployed, the stylet-like shaping element preferably forces the second portion 34 to adopt its spirally curved configuration so positioning the second portion 34 relatively close to the inner wall of the cochlea 12.

In this embodiment, it is envisaged that the stylet-like shaping element would remain in place within the second portion following implantation of the device. It is envisaged that in this embodiment, the second portion would be relatively thinner in size, than a second portion that otherwise preferentially adopts a curved configuration following deployment as described above.

An embodiment of a device that is constructed to control the extent of deployment of the second portion into the implantee from the first portion is depicted generally as 50 in FIGS. 5a and 5b. In this embodiment, the first portion 51 comprises a tube with the inner diameter of the tube decreasing towards its distal end 52 over a portion of the length of the tube adjacent its distal end 52. In the depicted embodiment, the inner diameter of the tube smoothly tapers towards the distal end 52. In this embodiment, the diameter of the depicted second portion 53 expands at a predetermined location spaced from the distal end 54 of the second portion 53. In this way, the second portion 53 is free to be deployed from the first portion 51 until frictional engagement between the expanded diameter of the second portion 53 and the tapering constriction of the tube prevents further deployment.

This increase in frictional engagement should be able to be felt by the surgeon implanting the device 50 and so inform the surgeon that maximum insertion depth of the second portion 53 has been reached. The second portion 53 can have one or more markers, such as visual markers, on its outer wall to also provide an indication of the depth of insertion of the second portion 53 relative to the first portion 51 into the cochlea 12.

In the depicted embodiments, a lumen is not required in the second portion of the elongate member to ensure appropriate implantation of the device. Despite this, the second portion can be provided with a lumen if desired. The lumen can extend from an opening in the second portion for at least some distance into the second portion. In one embodiment, the lumen can extend from an opening positioned at or adjacent the proximal end of the second portion through the second portion.

Such a lumen can be used as a channel or reservoir for the delivery of bioactive substances into the cochlea of the implantee. In one embodiment, the bio-active substance in the reservoir can leach from the lumen into the surrounding material of the second portion and eventually migrate out of the device to the desired site of action for the bio-active substance. In another embodiment, the second portion can have one or more substance egress means whereby the bio-active substance can move out of the lumen and through the body of the second portion to a position that is preferably close to the desired site of action for the bio-active substance.

Where the bio-active substance is carried in or comprises a fluid, each substance egress means preferably comprises a fluid egress means.

Each fluid egress means preferably has a valve means that allows fluid to exit the lumen but prevents, or at least substantially prevents, fluid flow from external the elongate member back into the lumen.

In a further embodiment, the proximal opening of the lumen can be in fluid communication with an additional reservoir for the bio-active substance that is external to the device. A pumping means, such as an osmotic pump, can transfer the bio-active substance from the additional reservoir into the lumen for subsequent delivery to the appropriate site of action.

It is also envisaged that the bio-active substance can be captured in the form of a solid pellet. An example of how this may occur is by impregnating the bio-active substance in a ceramic or a polymer pellet that has a predetermined rate of release of the bioactive substance. This solid pellet can then be stored in the lumen reservoir or in an external reservoir connectable to the lumen.

In one embodiment, the bioactive substance can comprise a steroid. In another embodiment, the bioactive substance can perform a function of reducing the resting neuron potential of neurons within the cochlea. The use of such substances can result in less energy being required to excite the neurons and cause stimulation. In yet another embodiment, the bioactive substance can comprise a nerve growth factor and mimetics to enhance the survival and growth of the nerve cells in the cochlea to improve the performance of the cochlear implant.

As the lumen is not necessarily required for implantation of the device, the osmotic pump and tube connecting the pump to the lumen can be mounted to the lumen at the time of manufacture of the device. This has the potential advantage of ensuring no connections need be made between the pump, the tube, and/or the opening in the lumen at the time of implantation of the device. This simplifies the surgery and also reduces the likelihood of inappropriate or inadequate installation of the pump to the lumen.

Figure 6A:
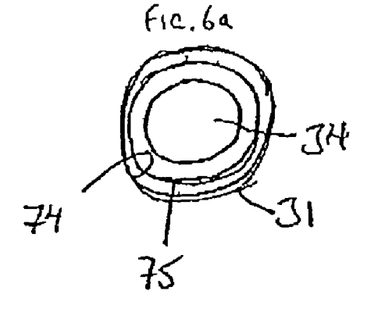
FIGS. 6a, 6b, 7a, 7b, 8a, and 8b depict alternative arrangements for minimising the friction between the first and second portions of the device according to embodiments of the present invention.

As discussed, the second portion is preferably free to be moved relative to the first portion, at least until maximum insertion depth is reached as described above. The surface of the first portion and/or the surface of the second portion that could come into contact with each other during desired movement of the second portion can be coated with a lubricious material. Where the first portion 31 is a tube, as is depicted in FIG. 6a, the inner surface 74 of the tube and/or the outer surface 75 of the second portion 34 can be coated with the lubricious material.

The lubricious material preferably becomes lubricious on being brought into contact with a fluid, such as a saline solution. Still further, the coating preferably becomes lubricious on being brought into contact with a body fluid, such as cochlear fluid.

In one embodiment, the lubricious material is selected from the group consisting of polyacrylic acid (PAA), polyvinyl alcohol (PVA), polylactic acid (PLA) and polyglycolic acid (PGA). It is envisaged that other similar materials could also be used.

In the embodiments depicted in FIGS. 6b-8b, the contact area between the surface of the first portion and the surface of the second portion is minimised to reduce the friction between the surfaces and so allow relatively free movement of the second portion, until at least the desired maximum extent of insertion of the second portion is reached.

Figure 6B:
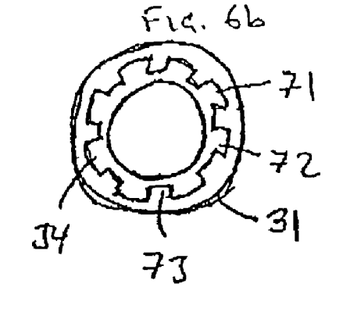

In FIG. 6b, a portion of the outer surface 71 of the second portion 34 comprise a series of ridges 72 and grooves 73.

Figures 7A, 7B:
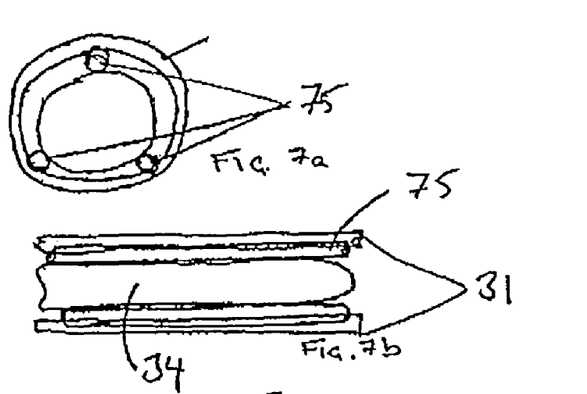

In FIGS. 7a and 7b, the role of the ridges is instead provided by a number of separate guidewires 75 extending longitudinally and positioned between the inner surface of the tubular first portion 31 and the outer surface of the second portion 34.

Figure 8A:
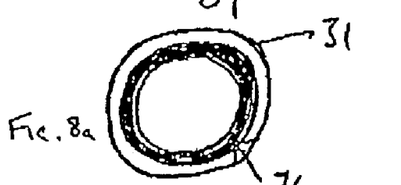
Figure 8B:
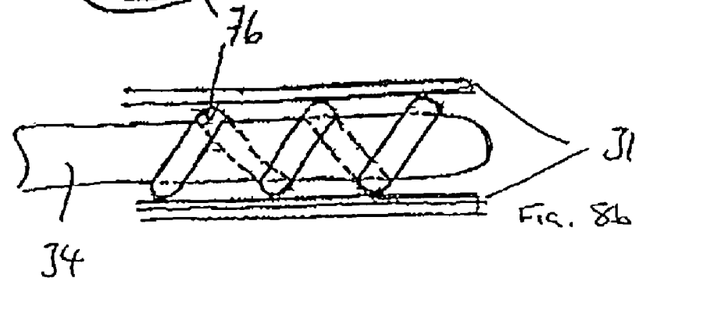

In FIGS. 8a and 8b, a guidewire 76 extends spirally through the device between the inner surface of the tubular first portion 31 and the outer surface of the second portion 34.

Where the first and second portions have a plurality of electrodes, the electrodes are preferably axially aligned along these portions. In a further embodiment, the axial alignment of the electrodes of the second portion substantially matches that of the electrodes on the first portion. In this regard, a guide means can be provided to ensure that the respective sets of electrodes of the two portions are aligned following deployment. For example, the inner surface of the tubular first portion may have a ridge or groove that is adapted to engage a corresponding complementary groove or ridge on the outer surface of the second portion.

Once implanted, the one or more electrodes mounted on the member, if present, can receive stimulation signals from a stimulator device, like stimulator and receiver unit 22 depicted in FIG. 1. Where the first portion is a tube and has one or more electrodes mounted thereon, the wires extending from these electrodes are preferably encapsulated within the wall of the tube and extend at least back to the proximal end thereof. This results in the interior of the tube being free to receive the second portion without interference from the wires. The manufacturing can be made in accordance with the method described in U.S. Pat. No. 5,720,099, the contents of which are incorporated herein by reference.

The stimulator and receiver unit 22 is positioned within a housing that is implanted within the bony well in the bone behind the ear 11 posterior to the mastoid.

The stimulator and receiver unit comprises a receiver coil 23 adapted to receive radio frequency (RF) signals from a corresponding transmitter coil 24 worn externally of the body. The radio frequency signals can comprise frequency modulated (FM) signals. The stimulator and receiver unit 22 can transmit signals to the transmitter coil 24 which receives the signals.

The transmitter coil 24 is held in position adjacent the implanted location of the receiver coil 23 by way of respective attractive magnets mounted centrally in, or at some other position relative to, the coils.

The external component comprises a speech processor 29 adapted to receive signals output by microphone 27. During use, the microphone 27 is preferably worn on the pinna of the implantee, however, other suitable locations can be envisaged, such as a lapel of the implantee's clothing. The speech processor 29 encodes the sound detected by the microphone 27 into a sequence of electrical stimuli following given algorithms, such as algorithms already developed for cochlear implant systems. The encoded sequence is transferred to the implanted receiver and stimulator unit 22 using the transmitter and receiver coils. The implanted stimulator and receiver unit 22 demodulates the FM signals and allocates the electrical pulses to the appropriate attached electrode by an algorithm which is consistent with the chosen speech coding strategy.

The external component further comprises a power supply. The power supply can comprise one or more rechargeable batteries. The transmitter and receiver coils are used to provide power via transcutaneous induction to the implanted stimulator and receiver unit and the electrode array.

While the implant system can rely on external componentry, in another embodiment, the controller, including the microphone 27, speech processor 29 and power supply can also be implantable. In this embodiment, the controller can be contained within a hermetically sealed housing or the housing used for the receiver and stimulator unit 22.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A cochlear implant device comprising an elongate member having:
    a first portion having a proximal end, a distal end, and at least one electrode supported thereon, the first portion being insertable into the cochlea of an implantee; and
    at least one second portion having a proximal end, a distal end, and at least one electrode supported thereon;
    wherein, on or following insertion of the first portion into the implantee, the second portion is positionable through and supported by the first portion;
    and further wherein, during or after insertion of the first portion, the second portion is still further movable relative to the first portion such that the distal end of the second portion is moved away from the proximal end of the first portion.

2. The cochlear implant device of claim 1 wherein the first portion of the elongate member is supported by the wall of the cochlea of the implantee.

3. The cochlear implant device of claim 1 wherein the first portion of the elongate member is substantially straight.

4. The cochlear implant device of claim 1 wherein the first portion of the elongate member comprises a substantially tubular member.

5. The cochlear implant device of claim 4 wherein the diameter of the tubular first portion decreases at least adjacent its distal end and wherein the diameter of the second portion increases at a predetermined location spaced from the distal end of the second portion to thereby provide a region of frictional engagement between said first and second portions of the elongate member as the distal end of the second portion is moved relatively away from the proximal end of the tubular first portion.

6. The cochlear implant device of claim 1 wherein the shape or configuration of the first portion of the elongate member does not substantially change on or following insertion of said first portion.

7. The cochlear implant device of claim 1 wherein the second portion of the elongate member is preformed such that at least a region thereof extending back from the distal end adopts a different configuration to that of the first portion during or after insertion of the first portion of the elongate member.

8. The cochlear implant device of claim 7 wherein said at least a region of the second portion adopts a curved configuration during or after insertion of the first portion of the elongate member.

9. The cochlear implant device of claim 1 wherein the second portion of the elongate member has a channel or reservoir for the delivery of at least one bioactive substance to the cochlea.

10. The cochlear implant device of claim 1 wherein more than one electrode is provided on both the first portion and the second portion of the elongate member.

11. The cochlear implant device of claim 10 wherein the alignment of the electrodes on the second portion substantially matches that of the electrodes on the first portion.

* * * * *